United States Patent
Park et al.

(10) Patent No.: US 11,344,209 B2
(45) Date of Patent: May 31, 2022

(54) ELECTRONIC DEVICE AND METHOD OF ESTIMATING BIO-INFORMATION USING THE SAME

(71) Applicant: SAMSUNG ELECTRONICS CO., LTD., Suwon-si (KR)

(72) Inventors: Sang Yun Park, Hwaseong-si (KR); Jae Min Kang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 398 days.

(21) Appl. No.: 16/439,869

(22) Filed: Jun. 13, 2019

(65) Prior Publication Data
US 2020/0146565 A1    May 14, 2020

(30) Foreign Application Priority Data
Nov. 13, 2018    (KR) .................. 10-2018-0138834

(51) Int. Cl.
*A61B 5/021*    (2006.01)
*A61B 5/00*    (2006.01)
(Continued)

(52) U.S. Cl.
CPC ........ *A61B 5/02108* (2013.01); *A61B 5/6843* (2013.01); *A61B 5/6898* (2013.01);
(Continued)

(58) Field of Classification Search
CPC . A61B 5/02108; A61B 5/6843; A61B 5/6898; A61B 5/0077; A61B 5/02007;
(Continued)

(56) References Cited

U.S. PATENT DOCUMENTS 7,179,228 B2    2/2007  Banet
7,691,068 B2    4/2010  Felder et al.
(Continued)

FOREIGN PATENT DOCUMENTS

JP    WO2015/115114 A1    8/2015
KR    10-2006-0081178 A    7/2006
(Continued)

OTHER PUBLICATIONS

Gilbertson, Brett. How does the Wacom Tablet PC Pen Work? Jul. 19, 2013 (Year: 2013).*
(Continued)

*Primary Examiner* — Sean P Dougherty
*Assistant Examiner* — Alexander H Connor
(74) *Attorney, Agent, or Firm* — Sughrue Mion, PLLC

(57) ABSTRACT

An electronic device for estimating bio-information is provided. According to one embodiment, the electronic device may include a pulse wave sensor configured to measure a pulse wave signal from an object; a magnetic field detector configured to detect a change in a magnetic field generated by a magnetic field source according to a change in a force exerted by the object to the pulse wave sensor; and a processor configured to acquire a contact pressure between the object and the pulse wave sensor based on the change in the magnetic field and obtain bio-information based on the pulse wave signal and the contact pressure.

23 Claims, 12 Drawing Sheets

(51) Int. Cl.
*A61B 5/02* (2006.01)
*A61B 5/1171* (2016.01)
*A61B 5/16* (2006.01)

(52) U.S. Cl.
CPC ......... *A61B 5/0077* (2013.01); *A61B 5/02007* (2013.01); *A61B 5/1176* (2013.01); *A61B 5/165* (2013.01); *A61B 5/442* (2013.01); *A61B 5/7425* (2013.01)

(58) Field of Classification Search
CPC ....... A61B 5/1176; A61B 5/165; A61B 5/442; A61B 5/7425; A61B 5/6826; A61B 5/02241; A61B 5/681; A61B 5/6803; A61B 5/0214; A61B 5/02438; A61B 5/749; A61B 5/7405; A61B 5/742; A61B 5/7455; A61B 5/05
See application file for complete search history.

(56) References Cited

U.S. PATENT DOCUMENTS

| | | | |
|---|---|---|---|
| 8,814,800 | B2 | 8/2014 | Fortin et al. |
| 2013/0005310 | A1 | 1/2013 | Lim et al. |
| 2018/0184923 | A1 | 7/2018 | Tai et al. |
| 2018/0335359 | A1* | 11/2018 | Eckinger ............... G01L 9/0072 |
| 2019/0008399 | A1* | 1/2019 | Mukkamala ....... A61B 5/02225 |
| 2019/0357779 | A1 | 11/2019 | Park et al. |

FOREIGN PATENT DOCUMENTS

| | | |
|---|---|---|
| KR | 10-2008-0054855 A | 6/2008 |
| KR | 10-1008139 B1 | 1/2011 |
| KR | 10-1264168 B1 | 5/2013 |
| WO | 2006/089763 A1 | 8/2006 |
| WO | 2017/152098 A1 | 9/2017 |

OTHER PUBLICATIONS

De Ridder B, Van Rompaey B, Kampen JK, Haine S, Dilles T. Smartphone Apps Using Photoplethysmography for Heart Rate Monitoring: Meta-Analysis. JMIR Cardio. Feb. 27, 2018;2(1):e4. doi: 10.2196/cardio.8802. PMID: 31758768; PMCID: PMC6834218. (Year: 2018).*
Mukherjee, Amritanshu. What is MST and how does it make Samsung Pay unique? Jun. 27, 2017. Accessed with waybackmachine (Year: 2017).*
Liang, Rong-Hao. GaussSense: Attachable Stylus Sensing Using Magnetic Sensor Grid. Oct. 10, 2012 (Year: 2012).*
Samsung. 10 Sensors of Galaxy S5: Heart Rate, Finger Scanner and more. Apr. 23, 2014 (Year: 2014).*
Chandrasekhar, A., Kim, C. S., Naji, M., Natarajan, K., Hahn, J. O., & Mukkamala, R. (2018). Smartphone-based blood pressure monitoring via the oscillometric finger-pressing method. Science translational medicine, 10(431). (Year: 2018).*
Communication dated Apr. 2, 2020, issued by the European Patent Office in counterpart European Application No. 19208002.6.

* cited by examiner

ELECTRONIC DEVICE AND METHOD OF ESTIMATING BIO-INFORMATION USING THE SAME

CROSS-REFERENCE TO RELATED APPLICATION(S)

This application claims priority from Korean Patent Application No. 10-2018-0138834, filed on Nov. 13, 2018, in the Korean Intellectual Property Office, the entire disclosure of which is incorporated herein by reference in its entirety.

BACKGROUND

1. Field

Apparatuses and methods consistent with example embodiments relate to a technology of estimating bio-information in an electronic device, and more particularly, to cuffless blood pressure estimation.

2. Description of Related Art

Generally, as examples of methods of non-invasively measuring blood pressure without causing pain to the human body, there are a method of measuring blood pressure through cuff-based pressure measurement and a method of estimating blood pressure through pulse wave measurement without a cuff.

The cuff-based blood pressure measurement method may include a Korotkoff-sound method and an oscillometric method. In the Korotkoff-sound method, a cuff is wrapped around a patient's upper arm and inflated to a pressure above the patient's systolic blood pressure, to measure blood pressure by listening to sound produced from blood flow while the pressure in the cuff is dropping down. In the oscillometric method using an automated machine, an inflated cuff is placed around a patient's upper arm, and a pressure inside the cuff is continuously monitored by gradually reducing the cuff pressure, to measure blood pressure based on a point where a large change occurs in the pressure.

As cuff-less blood pressure measurement methods, there are generally a method of estimating blood pressure by calculating a pulse transit time (PTT) and a pulse wave analysis (PWA) method of estimating blood pressure by analyzing a pulse waveform.

SUMMARY

According to an aspect of an example embodiment, there is provided an electronic device including: a pulse wave sensor configured to measure a pulse wave signal from an object; a magnetic field detector configured to detect a change in a magnetic field generated by a magnetic field source according to a change in a force exerted by the object to the pulse wave sensor; and a processor configured to acquire a contact pressure between the object and the pulse wave sensor based on the change in the magnetic field and obtain bio-information based on the pulse wave signal and the contact pressure.

The magnetic field source may include at least one of a permanent magnet and an electromagnet.

The magnetic field source may be mounted on a device separately provided from the electronic device. The device including the magnetic field source may be adapted to be placed on the object in opposition to a contact surface of the object and the pulse wave sensor, and to press the object against the contact surface of the object and the pulse wave sensor.

The electronic device may further include the magnetic field source.

The magnetic field source may be mounted in the electronic device and may support a magnetic secure transmission (MST) scheme.

The pulse wave sensor may include a photoplethysmography (PPG) sensor including a light source configured to emit light to the object and a detector configured to detect the light scattered or reflected from the object.

The pulse wave sensor may use at least one of a natural light, a light emitted from a display panel of the electronic device, and a flash light as a light source and may use at least one of a face recognition sensor, a camera, an illuminance sensor, and an iris recognition sensor as a detector.

In response to receiving a request for obtaining the bio-information, the processor may be further configured to generate guide information comprising at least one of action guide information for guiding a user's action to measure the pulse wave signal and pressure guide information for guiding a change of the contact pressure between the object and the pulse wave sensor.

The electronic device may further include an output interface configured to output the guide information, and a communication interface configured to transmit the guide information to an external device, wherein the processor may be further configured to control at least one of the output interface and the communication interface based on a position of the pulse wave sensor when the guide information is generated.

The processor may be further configured to convert the magnetic field detected at each measurement point in time into a contact pressure at each measurement point in time by using a predefined conversion model.

The processor may be further configured to acquire a statistical value including at least one of a sum, an average, and a minimum value of an X-axis value, a Y-axis value, and a Z-axis value of the magnetic field and convert the statistical value into the contact pressure by applying the statistical value to the predefined conversion model.

The processor may be further configured to acquire an oscillometric envelope that represents a relation between a pulse wave value of the pulse wave signal and the contact pressure at each measurement time point and obtain the bio-information based on the oscillometric envelope.

The processor may be further configured to acquire, as a feature value, at least one of a contact pressure value at a maximum amplitude point of the oscillometric envelope and contact pressure values having predetermined proportions of the contact pressure value at the maximum amplitude point, and obtain the bio-information based on the feature value.

The bio-information may include at least one of blood pressure, vascular age, a degree of arteriosclerosis, an aortic pressure waveform, a vascular compliance, a stress index, a degree of fatigue, a degree of skin elasticity, and skin age.

According to an aspect of another example embodiment, there is provided a method of estimating bio-information by an electronic device, including: measuring a pulse wave signal from an object, by a pulse wave sensor; detecting a change in a magnetic field by a magnetic field source according to a change in a force exerted by the object to the pulse wave sensor; acquiring a contact pressure between the object and the pulse wave sensor based on the change in the magnetic field; and obtaining bio-information based on the pulse wave signal and the contact pressure.

The method may further include, in response to a request for obtaining the bio-information, generating guide information including at least one of action guide information for guiding a user's action to measure the pulse wave signal and pressure guide information for guiding a change of the contact pressure between the object and the pulse wave sensor.

The acquiring the contact pressure may include converting the change in the magnetic field into a contact pressure by using a predefined conversion model.

The obtaining the bio-information may include acquiring an oscillometric envelope that represents a relation between a pulse wave value of the pulse wave signal and the contact pressure at each measurement time point, and obtaining the bio-information based on the oscillometric envelope.

The obtaining the bio-information may include acquiring, as a feature value, at least one of a contact pressure value at a maximum amplitude point of the oscillometric envelope and contact pressure values having predetermined proportions of the contact pressure value at the maximum amplitude point, and obtaining the bio-information based on the feature value.

According to an aspect of another example embodiment, there is provided an electronic device including: a pulse wave sensor configured to measure a pulse wave signal from a body part of a user when the user exerts a force to the pulse wave sensor by pressing the body part against the pulse wave sensor with a touch pen; a magnetic sensor configured to detect a change in a magnetic field generated by the touch pen according to a change in the force exerted by the body part to the pulse wave sensor; and a processor configured to acquire a contact pressure between the body part and the pulse wave sensor based on the change in the magnetic field and estimate blood pressure based on the pulse wave signal and the contact pressure.

The electronic device may further include a power supply configured to supply power to the touch pen using an electromagnetic induction scheme.

The processor may be further configured to generate guide information about the force exerted by the user to the pulse wave sensor and the contact pressure acquired based on the change in the magnetic field.

The processor may be further configured to estimate the blood pressure using oscillometry based on the contact pressure and the pulse wave signal.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
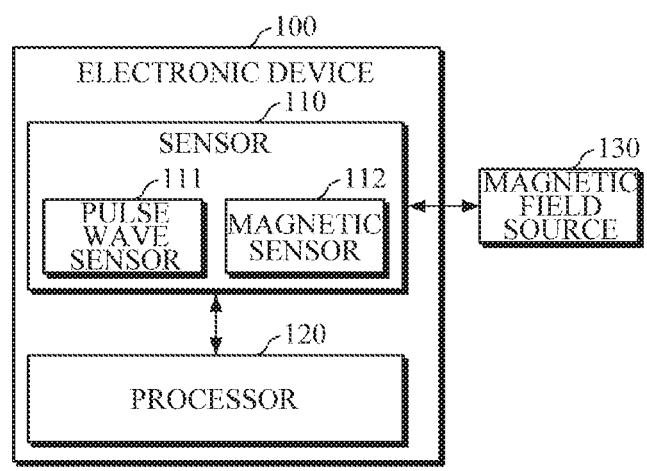
FIG. 1 is a block diagram illustrating an electronic device according to one example embodiment.

Example embodiments are described in greater detail below with reference to the accompanying drawings.

In the following description, like drawing reference numerals are used for like elements, even in different drawings. The relative size and depiction of these elements may be exaggerated for clarity, illustration, and convenience.

The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising" will be understood to imply the inclusion of stated elements but not the exclusion of any other elements. Terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an electronic device will be described in detail with reference to the accompanying drawings. The electronic device described hereinafter includes wearable devices manufactured in various forms, such as a smart watch, a smart band type, a headphone type, a hairband type, and the like, and mobile devices, such as a smartphone, a tablet personal computer (PC), and the like, but is not limited thereto.

FIG. 1 is a block diagram illustrating an electronic device according to one example embodiment.

Referring to FIG. 1, the electronic device 100 may include a sensor 110 and a processor 120. The sensor 110 may include a pulse wave sensor 111 and a magnetic sensor 112.

The pulse wave sensor 111 may measure a pulse wave signal from a user while the user places his/her finger on the pulse wave sensor 111 and changes a force exerted by the finger to the pulse wave sensor 111. The electronic device 100 may prompt the user to gradually increase or decrease the force exerted to the pulse wave sensor 111. For example, the pulse wave sensor 111 may measure a pulse wave signal while the user is gradually increasing the force for a predetermined period of time, thereby gradually increasing a contact pressure between the finger and the pulse wave sensor 111. In another example, the pulse wave sensor 111 may measure a pulse wave signal while the user is gradually reducing the force from a point where the force becomes equal to or higher than a threshold value, and thereby reducing the contact pressure.

The pulse wave sensor 111 may be a photoplethysmography (PPG) sensor including a light source configured to emit light to the user and a detector configured to detect light scattered or reflected from the object radiated by the light source according to characteristics of tissues of the user. However, the pulse wave sensor 111 is not limited thereto.

For example, the electronic device 100 may use, as the pulse wave sensor 111, various sensor modules that are mounted in the electronic device 100 and configured to measure physical quantity or monitor an operation status of the electronic device 100 and convert the measured or detected information into electric signals. In particular, the sensor modules may include a face recognition sensor, a camera module, an illuminance sensor, an iris recognition sensor, a flash, and a display panel. For example, natural light, light emitted from a display panel, or flash light may be used as a light source of the pulse wave sensor 111. The display panel may include a touch screen capable of receiving a touch input. In addition, a face recognition sensor, a camera, an illuminance sensor, or an iris recognition sensor may be used as a detector of the pulse wave sensor 111.

The magnetic sensor 112 may be mounted in the electronic device 100 and may acquire magnetic field information, such as information about the magnitude and/or direction of a magnetic field, which is generated by a magnetic field source 130. The magnetic sensor 112 may include a 2-axis or 3-axis geomagnetic sensor, a hall sensor configured to measure a magnetic flux density using a hall effect and output a voltage proportional to the magnetic flux density, a magneto-resistance (MR) sensor configured to measure a magnitude of a magnetic field using a fact that a magnetic resistance of an object varies according to a magnetic field, and a magneto-impedance (MI) sensor that applies a magneto impedance effect using a special amorphous wire.

The magnetic field source 130 may generate a magnetic field when the object is in contact with the pulse wave sensor 111 for measuring a pulse wave signal. The magnetic field source 130 may include a permanent magnet and/or an electromagnet. In one example, the magnetic field source 130 may be mounted in an object provided separately from the electronic device 100 as shown in FIG. 1. For example, the magnetic field source 130 may be mounted in a touch pen or a stylus pen, and configured to pressurize a body part (e.g., a finger) of the user that is to be in contact with the pulse wave sensor 111. The touch pen may be attachable to and detachable from a housing of the electronic device 100. In another example, the magnetic field source 130 may be mounted in an object adapted to be attached to or worn on the user. Alternatively, the magnetic field source 130 may be mounted or attached to an exterior, a housing, or a case, of the electronic device 100, or may be mounted on a wearable object. In another example, the magnetic field source 130 may be mounted in the electronic device 110 and may include, for example, a magnetic secure transmission (MST) sensor that supports magnetic secure transmission.

For example, when the user increases or reduces a force pressing the pulse wave sensor 111 in a state in which the user's finger is in contact with the pulse wave sensor 111 in order to measure a pulse wave signal, the shape of the finger and/or the distance between a top surface (e.g., a fingernail) of the finger and the magnetic sensor 112 is changed so that a change may occur in a magnetic field generated by the magnetic field source 130. The change may be also referred to as a change in a magnetic flux density. For example, when the distance between the magnetized finger and the magnetic sensor 112 is slightly reduced by strongly pressing the pulse wave sensor 111, a magnetic flux density is relatively increased.

As such, the magnetic sensor 112 may acquire the change in a magnetic flux density due to the change in the force of the finger pressing the pulse wave sensor 111.

Figure 2:
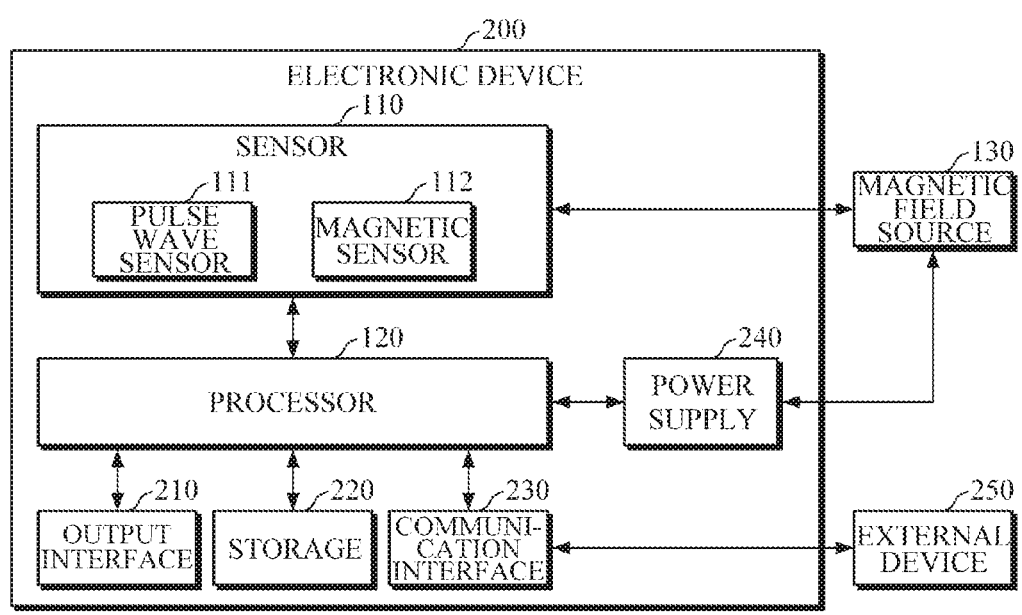
FIG. 2 is a block diagram illustrating an electronic device according to another example embodiment.

With reference to FIG. 2, the magnetic sensor 112 and the magnetic field source 130 are described as operating as a magnetic field detector and a magnetic field generator, respectively, but the example embodiment is not limited thereto. For example, the magnetic sensor 112 may generate and detect a magnetic field and the magnetic field source 130 may be omitted, or alternatively, the magnetic field source 130 may generate and detect a magnetic field and the magnetic sensor 112 may be omitted. In another example, both the magnetic sensor 112 and the magnetic field source 130 may generate and detect a magnetic field.

The processor 120 may acquire a contact pressure based on the change in the magnetic field acquired by the magnetic sensor 112, that is, the change in the magnetic flux density. For example, the processor 120 may apply a conversion model that represents a correlation between a magnetic flux density or a change in a magnetic flux density and a contact pressure to convert a magnetic flux density acquired at each measurement point in time into a contact pressure at each measurement point in time. When the magnetic sensor 112 is a 2-axis or 3-axis sensor, the processor 120 may convert a statistical value, such as a sum, an average, a maximum value, or a minimum value of 2-axis or 3-axis magnetic flux densities, or a value obtained using a predefined linear/nonlinear function into a contact pressure by applying a conversion model.

When the contact pressure is acquired, the processor 120 may estimate bio-information using the pulse wave signal measured by the pulse wave sensor 111 and the contact pressure. In particular, the bio-information may include one or more of blood pressure, vascular age, a degree of arteriosclerosis, an aortic pressure waveform, a vascular compliance, a stress index, a degree of fatigue, a degree of skin elasticity, and skin age. For example, the processor 120 may estimate blood pressure using oscillometry based on the contact pressure and the pulse wave signal. The processor 120 may acquire an oscillometric envelope based on the contact pressure and the pulse wave signal, extract a feature value for estimating bio-information from the acquired oscillometric envelope, and estimate the bio-information.

FIG. 2 is a block diagram illustrating an electronic device according to another example embodiment.

Referring to FIG. 2, the electronic device 200 according to the present embodiment may include a sensor 110, a processor 120, an output interface 210, a storage 220, a communication interface 230, and a power supply 240. The power supply 240 can be omitted according to a type of an object in which a magnetic field source 130 is mounted.

The sensor 110 may include a pulse wave sensor 111 and a magnetic sensor 112 as described above. The pulse wave sensor 111 may be a separate sensor for measuring a PPG signal. Alternatively, various sensor modules mounted in the electronic device 200 may be used as the pulse wave sensor 111, and a detailed description thereof will be omitted.

The processor 120 may generate guide information for measuring a pulse wave and provide the guide information to the user when a request for estimating bio-information is received from a user or an external device 250 or when a predetermined interval is reached.

In particular, the guide information may include action guide information for guiding the user to take an action necessary to measure a pulse wave from the user. For example, the action guide information may include a guidance voice, text, and/or a visual image to inform that the measurement of pulse wave will be initiated. Alternatively, the action guide information may include a voice, text, and/or a visual image to guide a position of the pulse wave sensor 111 with which the object is brought into contact. Alternatively, in a case where a magnetic field source 130 is mounted in an object, such as a touch pen, a visual image showing that the object is pressing a body part of the user may be provided.

Alternatively, the guide information may include pressure guide information to guide the user to change a contact pressure between the pulse wave sensor 111 and the user to be increased to or reduced. For example, the pressure guide information may include information about a reference contact pressure for guiding the user to gradually increase the contact pressure in a state in which the object is in contact with the pulse wave sensor 111 or for guiding the user to gradually reduce the contact pressure in a state in which the contact pressure greater than or equal to a predetermined threshold pressure is initially applied to the pulse wave sensor 111. The information about a reference contact pressure may include a reference contact pressure value at each point in time or a range of the reference contact pressure. In addition, the pressure guide information may include an actual contact pressure value obtained using the magnetic field information obtained by the magnetic sensor 112.

When the guide information is generated, the processor 120 may simultaneously or individually control the output interface 210 or the communication interface 230 so that the electronic device 200 and the external device 250 can concurrently or individually output the guide information.

For example, the processor 120 may control at least one of the output interface 210 and the communication interface 230 in consideration of a position of the pulse wave sensor 111. In a case in which the pulse wave sensor 111 is placed on a front side of the electronic device 200 and the user can view a display on the front side of the electronic device 200, the processor 120 may control the output interface 210 so that the guide information can be visually output on the display. In addition, in a case in which the pulse wave sensor 111 is placed on a rear side of the electronic device 200 and thus the user cannot view the display on the front side of the electronic device 200, the processor 120 may control the communication interface 230 to connect with the external device 250, for example, a wearable device, a tablet PC, a computer monitor, a smart TV, or the like, in a wired/wireless manner, and may transmit the guide information to the external device 250 to be output to the user.

In addition, the processor 120 may simultaneously control the output interface 210 and the communication interface 230 to concurrently output the guide information to the electronic device 200 and the external device 250. For example, in a case in which the user cannot view a front display of the electronic device 200, the processor 120 may output voice guide information using a voice output means (e.g., a speaker) of the electronic device 200 and simultaneously transmit visual guide information to the external device 250 to be visually output. However, the example embodiment is not limited to the above-described example.

The output interface 210 may output processing results of the pulse wave sensor 111, the magnetic sensor 112, and the processor 120. For example, the output interface 210 may visually output the guide information and/or an estimated bio-information value to the display panel or output the same through a speaker module or a haptic module in a non-visual way, such as vibration or tactile sensation. An area of the display may be divided into two or more sections. The pulse wave signal and the contact pressure used to estimate the bio-information may be output to a first section in the form of a graph and the estimated bio-information value may be output to a second section. In particular, when the estimated bio-information value deviates from a normal range, warning information may also be output in various ways, such as being emphasized in red color, being output along with the normal range, being output as a voice warning message, being output as intensity-controlled vibration, and the like.

The storage 220 may store the processing results of the pulse wave sensor 11, the magnetic sensor 112, and the processor 120. In addition, the storage 220 may store a variety of reference information necessary for estimating bio-information. For example, the reference information may include user characteristic information, such as user's age, sex, health status, and the like. In addition, the reference information may include a bio-information estimation model, bio-information estimation criteria, information about the reference contact pressure, and the like. However, the reference information is not limited to the above examples.

Examples of the storage 220 may include a storage medium, such as a memory of flash memory type, hard disk type, multimedia card micro type, or card type (e.g., SD or XD memory), random access memory (RAM), static random access memory (SRAM), read-only memory (ROM), electrically erasable programmable read-only memory (EEPROM), programmable read-only memory (PROM), magnetic memory, magnetic disk, optical disk, or the like, but is not limited thereto.

The communication interface 230 may communicate with the external device 250 using a wired/wireless communication technology under the control of the processor 120 and may transmit and receive a variety of data to and from the external device 250. For example, the communication interface 230 may transmit a bio-information estimation result to the external device 250 and may receive a variety of reference information necessary for estimating the bio-information from the external device 250. Examples of the external device 250 may include an information processing device, such as a cuff-type blood pressure measurement device, a smartphone, a tablet PC, a desktop PC, and a notebook PC. In addition, the communication interface 230 may transmit the guide information to the external device 250.

The communication technology may include Bluetooth communication, Bluetooth low energy (BLE) communication, near field communication (NFC), a wireless local area network (WLAN) communication, ZigBee communication, infrared data association (IrDA) communication, Wi-Fi direct (WFD) communication, ultra-wideband (UWB) communication, Ant+ communication, WiFi communication, radio frequency identification (RFID) communication, 3rd generation (3G) communication, 4G communication, 5G communication, etc. However, the communication technology is not limited to the above examples.

The power supply 240 may supply power to each configuration of the electronic device 200. The power supply 240 may supply power to a touch pen if the magnetic field source 120 is mounted in the touch pen. In particular, the power supply 240 may supply power to the touch pen using an electromagnetic induction scheme. However, the power supply 240 is not limited to the above examples.

Figure 3:
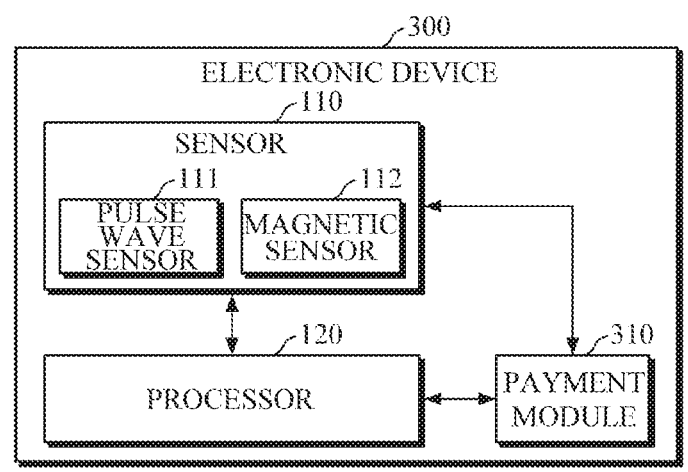
FIG. 3 is a block diagram illustrating an electronic device according to still another example embodiment.

FIG. 3 is a block diagram illustrating an electronic device according to still another example embodiment.

Referring to FIG. 3, the electronic device 300 according to the present embodiment may further include a payment module 310 in addition to the configurations in accordance with the example embodiment of FIG. 1 or 2.

The payment module 310 of the present example embodiment may include an magnetic secure transmission (MST) sensor that supports magnetic secure transmission, as a module to make, for example, a smartphone-based electronic payment.

The payment module 310 may generally support a hardware-based easy payment and may serve a function as a magnetic field source as described above for estimating bio-information. However, the example embodiment is not limited thereto, and the magnetic sensor 112 and the payment module 310 may be integrated into a single module or device. For example, the magnetic sensor 112 may include a magnetic field source (or a magnetic field generator) and a magnetic field detector. The magnetic field source may generate a magnetic field when a user touches the electronic device 300, and the magnetic field detector may detect a change in the magnetic field that is caused by a chance in a contact pressure between the user and the electronic device 300.

Figure 4A:
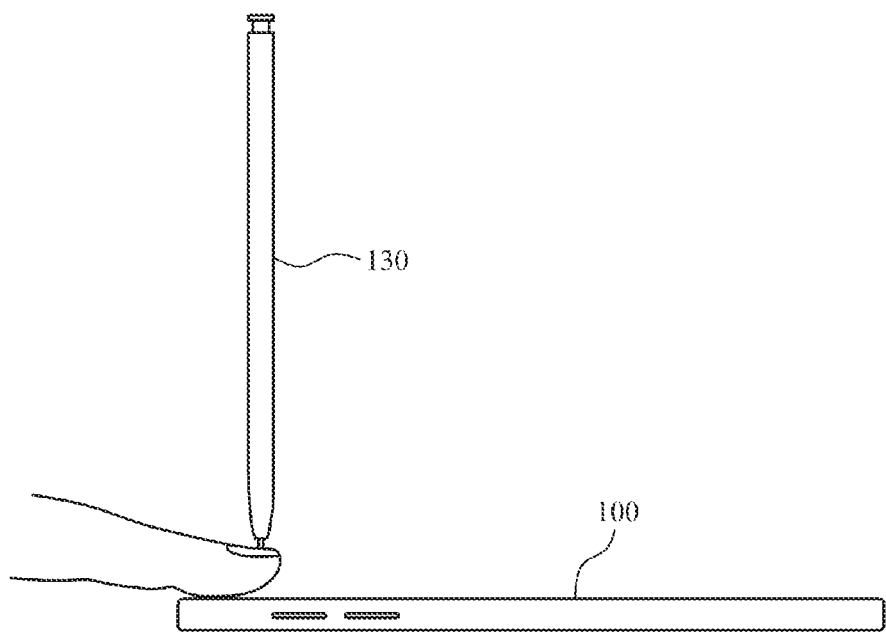
FIG. 4A is a diagram for describing a method of pressurizing an object with a touch pen.
Figure 4B:
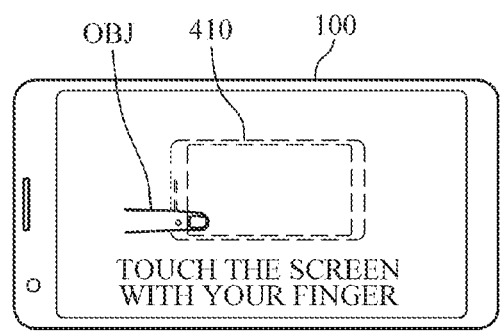
FIG. 4B is a diagram for describing an action guide for measuring a pulse wave signal.

FIG. 4A is a diagram for describing a method of pressurizing an object with a touch pen. FIG. 4B is a diagram for describing an action guide for measuring a pulse wave signal. A description will be given with reference to FIGS. 1 to 4B.

Referring to FIG. 4A, the user may place his/her finger on the electronic device 100, place a touch pen 130 vertically on the fingernail of the finger, and then press the finger against the electronic device 100 using the touch pan 130. The touch pen 130 may generate a magnetic field. At this time, a contact pressure between the finger and the electronic device 100 may be changed by a force pressing the user's finger with the touch pen 130.

Referring to FIG. 4B, the processor 120 may generate action guide information 410 in response to a request for estimating bio-information and output the action guide information 410 to the display of the electronic device 100. The action guide information may include, for example, an image showing a position at which the user's finger OBJ should touch. As shown in FIG. 4B, when the pulse wave sensor 111 uses the light from the display panel as a light source and a front camera as a detector, the processor 120 may guide the user to touch his/her finger on the front camera and a part of the display panel.

Meanwhile, the processor 120 may check whether the user touches a guided position with his/her finger. The processor 120 may display a moving image of a finger OBJ repeatedly touching and releasing the guided position as the action guide information 410 until the user's finger touches the correct position. However, this is merely an example, and the action guide information may be output in various ways by taking into account the position of the pulse wave sensor 111 or the like.

Figure 5A:
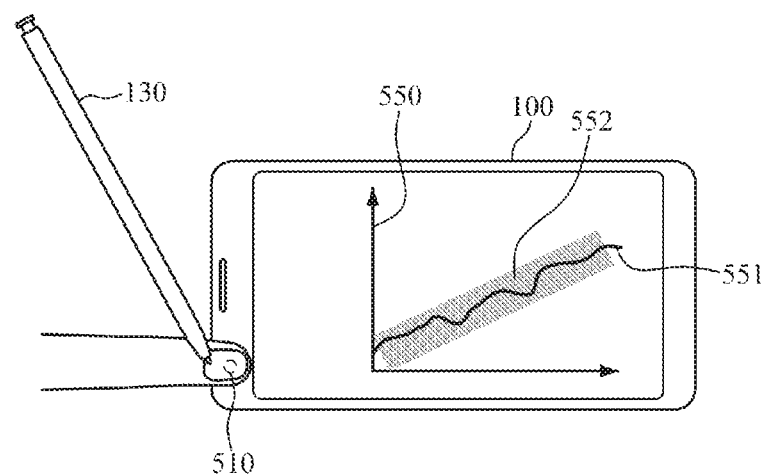
FIGS. 5A and 5B are diagrams for describing embodiments in which an electronic device provides a guide for a contact pressure.
Figure 5B:
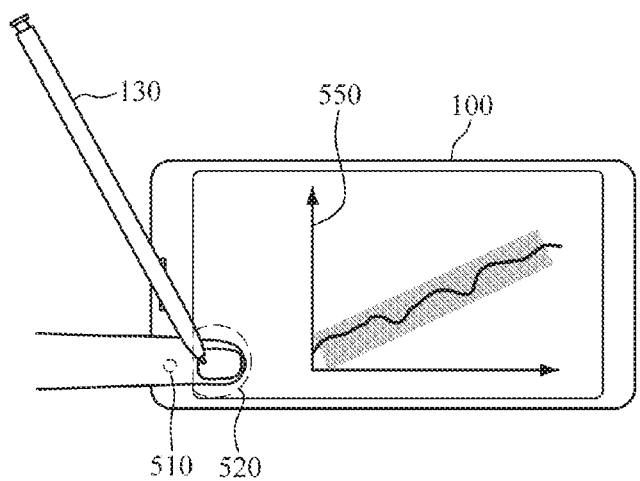

FIGS. 5A and 5B are diagrams for describing example embodiments in which an electronic device provides a guide for a contact pressure.

Referring to FIG. 5A, an example is illustrated in which a pulse wave sensor 111 uses natural light as a light source and a front camera module 510 of an electronic device 100 is used as a detector to measure a pulse wave signal. However, the example is not limited thereto, and a face recognition sensor, an illuminance sensor, and an iris recognition sensor which are located on the front side of the electronic device 100 may be used as a detector. As illustrated in FIG. 5A, a user touches the camera module 510 of the electronic device 100 with his/her finger, places a touch pen 130 vertically on the fingernail, and presses the fingernail in a direction perpendicular to the electronic device 100. At this time, the finger is magnetized by a magnetic field generated by the touch pen 120 and a magnetic sensor 112 of the electronic device 100 may detect a magnetic flux density that changes according to the finger.

In addition, a processor 120 of the electronic device 100 may provide the user with pressure guide information 550 through a display screen in order to guide a force pressing the fingernail using the touch pen 130. The processor 120 may refer to reference information and display a range 552 of a reference contact pressure that the user should apply to the camera module 510 by pressing the fingernail with the touch pen 130.

In addition, when a change of the magnetic field generated by the touch pen 130, that is, the magnetic flux density, is detected by the magnetic sensor 112, the processor 120 may convert the detected magnetic flux density into a contact pressure using a conversion model and display the acquired contact pressure as an actual contact pressure 551 of the guide information 550.

The camera module 510 may measure a pulse wave signal by detecting light reflected or scattered from the finger when surrounding natural light has been incident into the finger in a state where the finger is in contact with the camera module. The processor 120 may estimate blood pressure based on an oscillometric scheme applied to the measured pulse wave signal and the contact pressure at each measurement point in time.

FIG. 5B is a diagram illustrating an example in which part of light emitted from the display panel 520 is used as a light source and a camera module 510 placed on the front side of an electronic device 100 is used as a detector to measure a pulse wave signal and simultaneously pressure guide information is output to a display panel 520.

Referring to FIG. 5B, a user places his/her finger on the front camera module 510 and a part of the display panel 520 based on action guide information as described with reference to FIG. 4B, places a touch pen 130 vertically on a fingernail and presses the fingernail in a direction perpendicular to the electronic device 100. As described with reference to FIG. 5A, at this time, the processor 120 may output the pressure guide information 550 to the display panel 520.

Figure 6A:
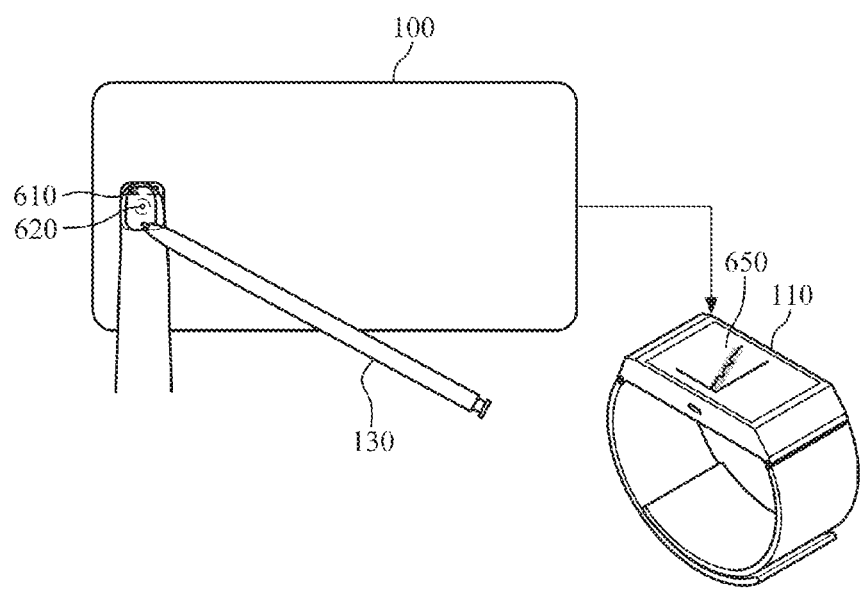
FIGS. 6A and 6B are diagrams for describing embodiments in which a guide for a contact pressure is provided through an external device.
Figure 6B:
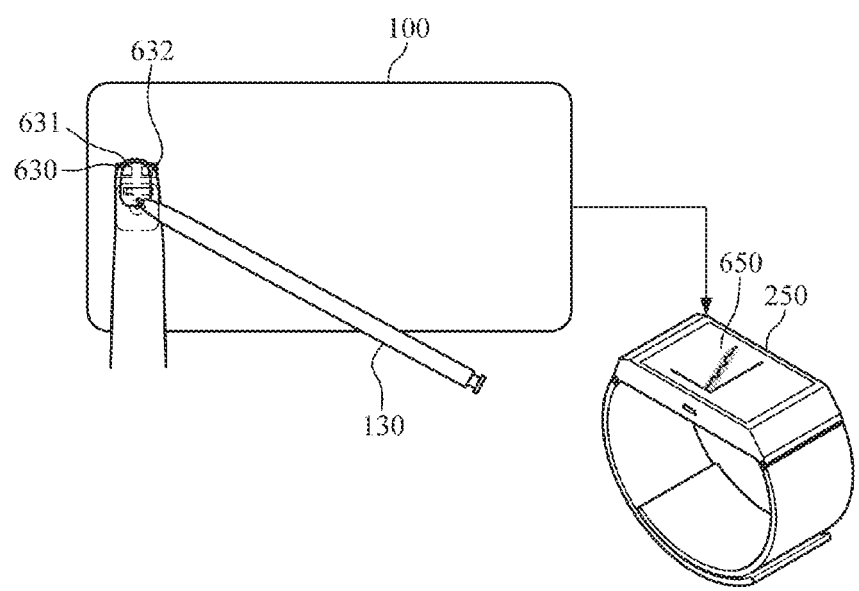

FIGS. 6A and 6B are diagrams for describing example embodiments in which a guide for a contact pressure is provided through an external device. As shown in FIGS. 6A and 6B, an example in which a pulse wave sensor 111 is placed on the rear surface of an electronic device 100 and a user cannot view a display on the front side of the electronic device 100 is illustrated.

FIG. 6A is a diagram illustrating an example in which a flash 610 placed on the rear surface of the electronic device 100 is used as a light source of the pulse wave sensor 111 and a camera module 620 is used as a detector of the pulse wave sensor 111. In particular, the user places his/her finger on the flash 610 and a camera 620 of the electronic device 100, places a touch pen 130 vertically on a fingernail and presses the fingernail in a direction perpendicular to the electronic device 100.

FIG. 6B is a diagram illustrating an example in which a pulse wave signal is measured using a PPG sensor 630 which is separately installed on a rear surface of the electronic device 100. The user places his/her finger on the pulse wave sensor 630 of the electronic device 100, places a touch pen 130 vertically on the fingernail and presses the fingernail in a direction perpendicular to the electronic device 100.

The PPG sensor 630 may include a light source 631 and a detector 632. For example, the light source 631 may be configured as a light emitting diode (LED), a laser diode, or a phosphor, and may emit visible light rays, near-infrared rays (NIRs), or mid-infrared rays (MIRs). However, the wavelength of light to be emitted from the light source may vary according to the purpose of measurement and the type of a component to be analyzed. In addition, the light source is not necessarily configured as a single light emitter and may be configured in the form of an array of a plurality of light emitters.

In addition, the detector 632 may be configured as a photodiode, a phototransistor (PTr), or a charge-coupled device (CCD), and may receive light reflected or scattered from an object. The detector 632 is not necessarily configured with one component and may be configured in the form of an array of a plurality of components.

Referring to FIGS. 6A and 6B, a processor 120 of the electronic device 100 may transmit action guide information and/or pressure guide information 650 to guide the user to press the fingernail using the touch pen 130 to the external device 250 (e.g., a smart watch) through a communication interface 230 and provide the information to the user. In this particular, the processor 120 of the electronic device 100 may also output voice pressure guide information, for example, voice information informing that an actual contact pressure deviates from a reference contact pressure range, using a voice output module (e.g., a speaker).

The processor 120 of the electronic device 100 may determine whether the user touches a sensor module (e.g., a front camera, an iris recognition sensor, a face recognition sensor) on the front side of the electronic device 100 or the PPG sensor on the rear side or a rear camera. When it is determined that the user is in contact with the rear PPG sensor, the processor 120 may control the communication interface 230 to build a communication connection with the external device 250 in vicinity and transmit guide information to the connected external device 250.

Figure 7A:
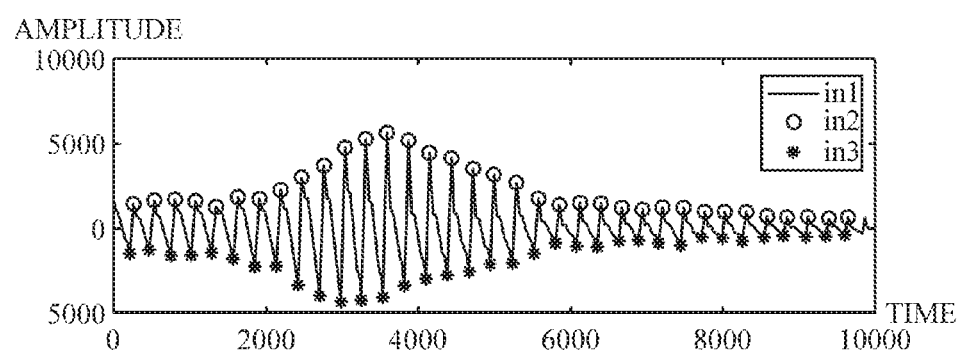
FIGS. 7A and 7B are graphs for describing oscillometric-based blood pressure estimation.
Figure 7B:
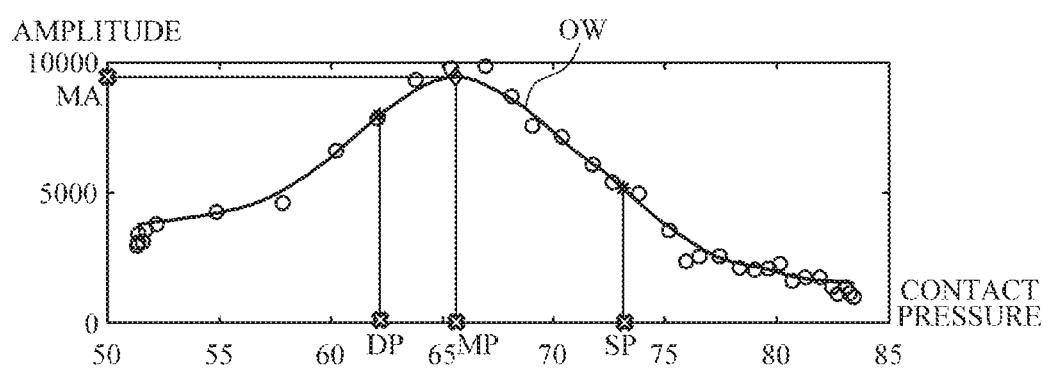

FIGS. 7A and 7B are graphs for describing oscillometric-based blood pressure estimation.

Referring to FIG. 7A, when a contact pressure is acquired based on magnetic field information detected by a magnetic sensor 112, a processor 120 may acquire an oscillometric envelope OW that represents an amplitude of a pulse wave versus a contact pressure based on a pulse wave signal measured by a pulse wave sensor 111. For example, the processor 120 may extract a peak-to-peak point by subtracting an amplitude value in3 at a minus (−) point from an amplitude value in2 at a plus (+) point of a waveform envelope in1 at each measurement time point of the pulse wave signal and acquire the oscillometric envelope OW by plotting the amplitude of the extracted peak-to-peak point at each measurement time point based on a contact pressure at the same measurement time point.

Referring to FIG. 7B, the processor 120 may acquire feature values for estimating blood pressure from the oscillometric envelope OW. The processor 120 may acquire, as feature values, an amplitude value MA at a maximum peak point, a contact pressure value MP at the maximum peak point, contact pressure values SP and DP that are on the left and right sides and predetermined proportions (e.g., 0.5 to 0.7) of the contact pressure value MP at the maximum peak point.

When the feature values are extracted, the processor 120 may estimate blood pressure by applying the extracted feature values to a predefined blood pressure estimation model. The blood pressure estimation model may be defined as various linear or nonlinear coupled function forms without any particular limitation, such as addition, subtraction, division, multiplication, logarithmic value, and regression equation. For example, Equation 1 below illustrates a simple linear function formula.

$$y = ax + b \quad (1)$$

Here, y denotes an estimated blood pressure value to be obtained and x denotes an extracted feature value. a and b are values obtained in advance through a preprocessing process and may be defined differently according to a type of blood pressure and a user characteristic. For example, the processor 120 may independently estimate mean blood pressure, diastolic blood pressure, and systolic blood pressure through Equation 1 in which coefficients a and b are differently defined for each of mean blood pressure, diastolic blood pressure, and systolic blood pressure. For example, mean blood pressure, diastolic blood pressure, and systolic blood pressure may be obtained by inputting the extracted feature values MP, DP, and SP to the equation that is defined for each type of blood pressure.

Figure 8:
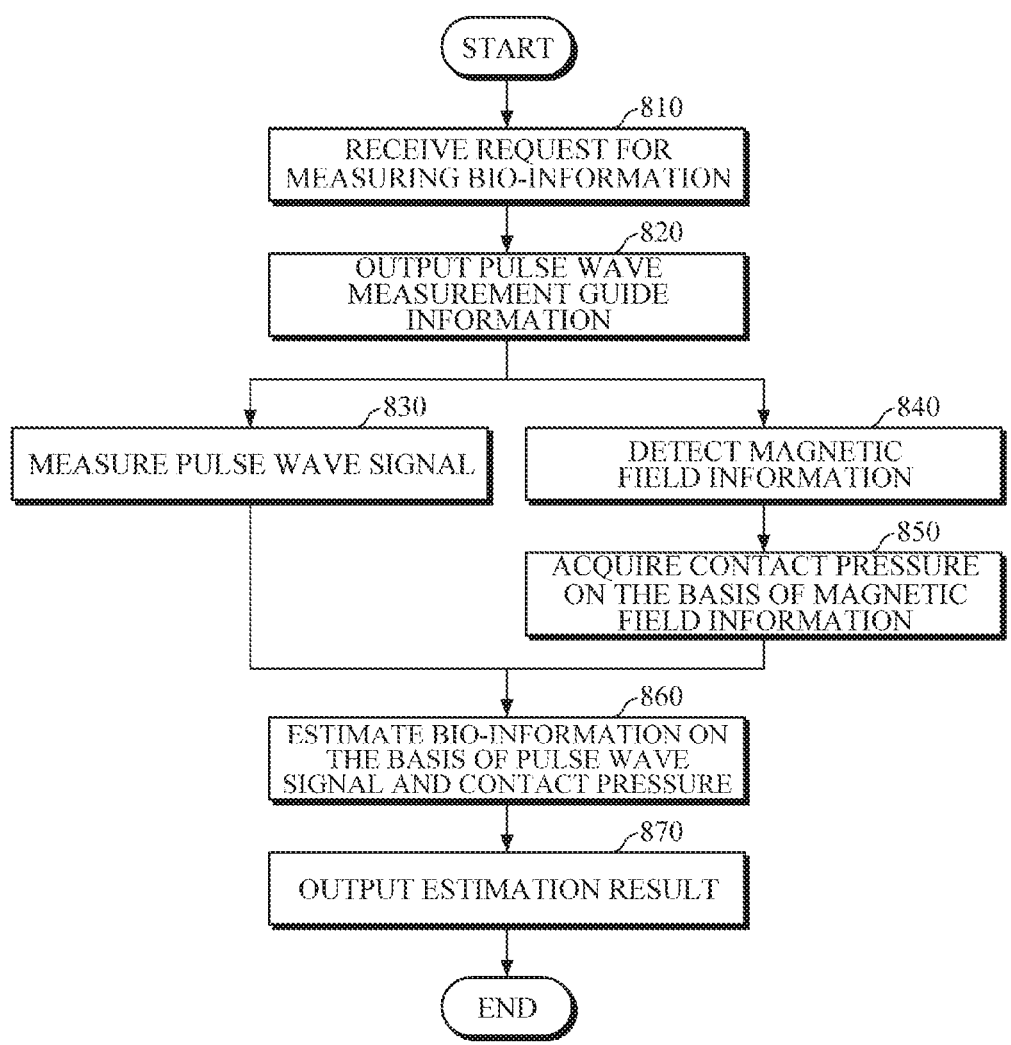
FIG. 8 is a flowchart illustrating a method performed by an electronic device to measure bio-information according to one example embodiment.

FIG. 8 is a flowchart illustrating a method performed by an electronic device to measure bio-information according to one example embodiment. FIG. 8 illustrates one example embodiment of a method performed by the electronic devices 100, 200, and 300 of FIGS. 1 to 3 to measure bio-information. Since described in detail above, the method will be described in brief to avoid redundancy.

First, when an electronic device 100/200/300 receives a request for estimating bio-information in operation 810, the electronic device 100/200/300 may output pulse wave measurement guide information in operation 820. The request for estimating bio-information may be received from a user or from an external device connected for communication. The example embodiment is not limited thereto, and it may be automatically determined that the request for estimating bio-information is received when a predetermined estimation interval is reached.

Then, the pulse wave measurement guide information may be output in operation 820. In particular, the guide information may include action guide information to guide a user's action for measuring a pulse wave and pressure guide information to guide a contact pressure between an object and a pulse wave sensor 111. The action guide information may include information about a position or direction of the pulse wave sensor 111 with which the object is to be in contact and the pressure guide information may include a reference contact pressure at which the user should press the pulse wave sensor 111 through the object and an actual contact pressure at which the object actually presses the pulse wave sensor 111. The electronic device 100/200/300 may output the guide information through a display or a speaker, and output simultaneously or solely the guide information to the external device.

Then, the user may bring the object into contact with the pulse wave sensor 111 for measuring a pulse wave and measure a pulse wave signal from the object while increasing or reducing the contact pressure for a predetermined period of time in operation 830.

In addition, magnetic field information generated by a magnetic field source 130 may be detected while a force of the object pressing the pulse wave sensor 111 for measuring the pulse wave is changed in operation 840. The magnetic field source 130 may be mounted in the electronic device 100/200/300 or be configured as a separate hardware object. For example, the magnetic field source 130 may be mounted on a touch pen and generate a magnetic field while the user is pressing the object with the touch pen. Alternatively, the magnetic field source 130 may be formed to be wearable on a finger or attachable to an exterior of the electronic device 100/200/300 or a case of the electronic device 100/200/300. Alternatively, an MST sensor, which is mounted in the electronic device 100/200/300 and supports an easy automatic payment of a smartphone, may be used as the magnetic field source 130.

As the object magnetized by a magnetic field generated by the magnetic field source 130 changes a force pressing the pulse wave sensor 111, the shape of the object is changed or a distance between the object and the magnetic sensor is slightly changed, so that a minute change in a magnetic flux density occurs. Such a change in the magnetic flux density may be detected by the magnetic sensor.

Then, a contact pressure between the object and the pulse wave sensor 111 at each point in time at which the pulse wave signal is measured may be acquired based on the detected magnetic field information in operation 850. For example, the contact pressure may be acquired from the change in a magnetic flux density detected at each point in time using a conversion model that defines a correlation between the change of magnetic flux density and the contact pressure.

In operation 860, bio-information may be estimated based on the pulse wave signal measured in operation 830 and the contact pressure acquired in operation 850. For example, an oscillometric envelope that represents an amplitude of a pulse wave versus a contact pressure at each point in time is obtained, and estimate blood pressure may be estimated using the obtained oscillometric envelope. For example, a contact pressure corresponding to a maximum amplitude of the oscillometric envelope may be obtained as a feature value for estimating a mean blood pressure and contact pressures that are on the left and right sides and predetermined proportions of the contact pressure value that corresponds to a maximum amplitude may be extracted as feature values for estimating diastolic blood pressure and systolic blood pressure. An estimated blood pressure value may be obtained by inputting the extracted feature value to a pre-defined blood pressure estimation equation.

Then, the bio-information estimation result may be output in operation 870. The electronic device 100/200/300 may output the bio-information estimation result in various ways using a display, a speaker module, a haptic device, and the like. In this case, warning information may also be output together with the bio-information estimation result. For example, when the estimated blood pressure deviates from a normal range, warning information that informs that the user's blood pressure is not within the normal range may be output in various ways, such as a different color, vibration, tactile sensation, and the like. In addition, the bio-information estimation result may be transmitted to the external device to be provided to the user.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An electronic device comprising:
   a photoplethysmography (PPG) sensor configured to measure a pulse wave signal from an object;
   a magnetic sensor configured to detect a change in a magnetic field generated by a magnetic field source according to a change in a force exerted by the object to the PPG sensor, while the object is placed between the PPG sensor and the magnetic field source; and
   a processor configured to acquire a contact pressure between the object and the PPG sensor based on the change in the magnetic field, while the object is placed between the PPG sensor and the magnetic field source, and obtain bio-information based on the pulse wave signal and the contact pressure.

2. The electronic device of claim 1, wherein the magnetic field source comprises at least one of a permanent magnet and an electromagnet.

3. The electronic device of claim 1, wherein the magnetic field source is detachable from a body of the electronic device, and
   wherein the magnetic field source is adapted to be placed on the object in opposition to a contact surface of the object and the PPG sensor, and to press the object against the contact surface of the object and the PPG sensor.

4. The electronic device of claim 1, wherein the electronic device further comprises the magnetic field source.

5. The electronic device of claim 1, wherein the magnetic field source is mounted in the electronic device and supports a magnetic secure transmission scheme.

6. The electronic device of claim 1, wherein the PPG sensor comprises a photoplethysmography sensor comprising a light source configured to emit light to the object and a light detector configured to detect the light scattered or reflected from the object.

7. The electronic device of claim 1, wherein the PPG sensor uses at least one of a natural light, a light emitted from a display panel of the electronic device, and a flash light as a light source and uses at least one of a face recognition sensor, a camera, an illuminance sensor, and an iris recognition sensor as a light detector.

8. The electronic device of claim 7, wherein, in response to receiving a request for obtaining the bio-information, the processor is further configured to generate guide information comprising at least one of action guide information for guiding an action of a user to measure the pulse wave signal and pressure guide information for guiding a change of the contact pressure between the object and the PPG sensor.

9. The electronic device of claim 8,
wherein the processor is further configured to display the guide information based on a position of the PPG sensor.

10. The electronic device of claim 1, wherein the processor is further configured to convert the magnetic field detected at each measurement point in time into the contact pressure at each measurement point in time by using a predefined conversion model.

11. The electronic device of claim 10, wherein the processor is further configured to acquire a statistical value including at least one of a sum, an average, and a minimum value of an X-axis value, a Y-axis value, and a Z-axis value of the magnetic field and convert the statistical value into the contact pressure by applying the statistical value to the predefined conversion model.

12. The electronic device of claim 1, wherein the processor is further configured to acquire an oscillometric envelope that represents a relation between a pulse wave value of the pulse wave signal and the contact pressure at each measurement time point and obtain the bio-information based on the oscillometric envelope.

13. The electronic device of claim 12, wherein the processor is further configured to acquire, as a feature value, at least one of a contact pressure value at a maximum amplitude point of the oscillometric envelope and contact pressure values having predetermined proportions of the contact pressure value at the maximum amplitude point, and obtain the bio-information based on the feature value.

14. The electronic device of claim 1, wherein the bio-information comprises at least one of blood pressure, vascular age, a degree of arteriosclerosis, an aortic pressure waveform, a vascular compliance, a stress index, a degree of fatigue, a degree of skin elasticity, and skin age.

15. A method of estimating bio-information by an electronic device, the method comprising:
measuring a pulse wave signal from an object, by a photoplethysmography (PPG) sensor;
detecting a change in a magnetic field by a magnetic field source according to a change in a force exerted by the object to the PPG sensor, while the object is placed between the PPG sensor and the magnetic field source;
acquiring a contact pressure between the object and the PPG sensor based on the change in the magnetic field, while the object is placed between the magnetic field source and the PPG sensor; and
obtaining bio-information based on the pulse wave signal and the contact pressure.

16. The method of claim 15, further comprising in response to a request for obtaining the bio-information, generating guide information comprising at least one of action guide information for guiding an action of a user to measure the pulse wave signal and pressure guide information for guiding a change of the contact pressure between the object and the PPG sensor.

17. The method of claim 15, wherein the acquiring the contact pressure comprises converting the change in the magnetic field into a contact pressure by using a predefined conversion model.

18. The method of claim 15, wherein the obtaining the bio-information comprises acquiring an oscillometric envelope that represents a relation between a pulse wave value of the pulse wave signal and the contact pressure at each measurement time point, and obtaining the bio-information based on the oscillometric envelope.

19. The method of claim 18, wherein the obtaining the bio-information comprises acquiring, as a feature value, at least one of a contact pressure value at a maximum amplitude point of the oscillometric envelope and contact pressure values having predetermined proportions of the contact pressure value at the maximum amplitude point, and obtaining the bio-information based on the feature value.

20. An electronic device comprising:
a photoplethysmography (PPG) sensor configured to measure a pulse wave signal from a body part of a user when the user exerts a force to the PPG sensor by pressing the body part against the PPG sensor with a touch pen;
a magnetic sensor configured to detect a change in a magnetic field generated by the touch pen according to a change in the force exerted by the body part to the PPG sensor, while the body part is placed between the touch pen and the PPG sensor; and
a processor configured to acquire a contact pressure between the body part and the PPG sensor based on the change in the magnetic field, while the body part is placed between the touch pen and the PPG sensor, and estimate blood pressure based on the pulse wave signal and the contact pressure.

21. The electronic device of claim 20, further comprising a power supply configured to supply power to the touch pen using an electromagnetic induction scheme.

22. The electronic device of claim 20, wherein the processor is further configured to generate guide information about the force exerted by the user to the PPG sensor and the contact pressure acquired based on the change in the magnetic field.

23. The electronic device of claim 20, wherein the processor is further configured to estimate the blood pressure using oscillometry based on the contact pressure and the pulse wave signal.

* * * * *